(12) United States Patent
Mortet et al.

(10) Patent No.: US 7,663,295 B2
(45) Date of Patent: Feb. 16, 2010

(54) METHOD AND SYSTEM FOR MEASURING PHYSICAL PARAMETERS WITH A PIEZOELECTRIC BIMORPH CANTILEVER IN A GASEOUS OR LIQUID ENVIRONMENT

(75) Inventors: Vincent Mortet, Kessel-Lo (BE); Rainer Petersen, St. Truiden Velm (BE)

(73) Assignee: IMEC, Leuven (BE)

( * ) Notice: Subject to any disclaimer, the term of this patent is extended or adjusted under 35 U.S.C. 154(b) by 202 days.

(21) Appl. No.: 11/610,976

(22) Filed: Dec. 14, 2006

(65) Prior Publication Data
US 2007/0138909 A1 Jun. 21, 2007

Related U.S. Application Data

(60) Provisional application No. 60/750,729, filed on Dec. 15, 2005.

(51) Int. Cl.
*H01L 41/04* (2006.01)
(52) U.S. Cl. .................. 310/338; 310/323.21; 310/336
(58) Field of Classification Search ......... 310/330–332, 310/338, 323.21, 336
See application file for complete search history.

(56) References Cited

U.S. PATENT DOCUMENTS

| 4,144,747 | A | 3/1979 | Datwyler |
| 4,554,927 | A | 11/1985 | Fussell |
| 5,089,695 | A | 2/1992 | Willson et al. |
| 5,379,639 | A | 1/1995 | Hulsing, II et al. |
| 5,458,000 | A | 10/1995 | Burns et al. |
| 5,511,427 | A | 4/1996 | Burns |
| 5,903,380 | A * | 5/1999 | Motamedi et al. ............ 359/224 |
| 6,781,285 | B1 * | 8/2004 | Lazarus et al. ............... 310/332 |
| 2002/0044327 | A1 * | 4/2002 | Fujita et al. .................. 359/224 |
| 2002/0182589 | A1 * | 12/2002 | Knudsen et al. ................. 435/4 |
| 2003/0032293 | A1 * | 2/2003 | Kim et al. .................... 438/694 |
| 2007/0089515 | A1 * | 4/2007 | Shih et al. ...................... 73/579 |

OTHER PUBLICATIONS

Rasmussen, P.A., et al., "Optimised Cantilever Biosensor With Piezoresistive Read-Out," Ultramicroscopy 97, (2003), pp. 371-376.
Sandberg, R., et al., "Temperature and Pressure Dependence of Resonance in Multi-Layer Microcantilevers," Journal of Micromechanics and Microengineering, 15 (2005), pp. 1454-1458.

(Continued)

*Primary Examiner*—Walter Benson
*Assistant Examiner*—Derek J Rosenau
(74) *Attorney, Agent, or Firm*—McDonnell Boehnen Hulbert & Berghoff LLP

(57) ABSTRACT

A piezoelectric bimorph cantilever is used for determining physical parameters in a gaseous or liquid environment. The sensor works as a driven and damped oscillator. Contrary to common cantilever sensor systems, the piezoelectric film of the bimorph cantilever acts as both a sensor and an actuator. Using at least two resonance mode of the bimorph cantilever, at least two physical parameters can be measured simultaneously in a gas or a liquid. An optimized piezoelectric cantilever and a method to produce the cantilever are also described.

12 Claims, 16 Drawing Sheets

OTHER PUBLICATIONS

Chen, G.Y. et al., "Resonance Response of Scanning Force Microscopy Cantilevers," Rev. Sci. Instrum., vol. 65, No. 8, Aug. 1994, pp. 2532-2537.

DeVoe, Don L., et al., "Modeling and Optimal Design of Piezoelectric Cantilever Microactuators," Journal of Microelectromechanical Systems, vol. 6, No. 3, Sep. 1997, pp. 266-270.

Wang, Zheyao, et al., "A Temperature Insensitive Quartz Resonator Force Sensor," Meas. Sci. Technol. 11 (2000), pp. 1565-1569.

Mertens, Johann, "Effects of Temperature and Pressure on Microcantilever Resonance Response," Ultramicroscopy 97 (2003), pp. 119-126.

Cullen, D.E., "Measurement of Saw Velocity Versus Strain For YX," Ultrasonics Symposium Proceedings, IEEE Cat. #75, CHO 994-4SU (1975), pp. 519-522.

Landau, L.D., et al., "Theory of Elasticity, $3^{rd}$ Edition," Institute of Physical Problems, USSR Academy of Sciences, Moscow USSR, pp. 99-103, Jan. 15, 1986.

* cited by examiner (1) Silicon (2) Si$_3$N$_4$ (3) SiO$_2$ (4) Photoresist (5) Diamond (6) Chromium (7) AlN (8) Al

A

B (1) amplification stage (2) Phase shift stage (3) Cantilever

METHOD AND SYSTEM FOR MEASURING PHYSICAL PARAMETERS WITH A PIEZOELECTRIC BIMORPH CANTILEVER IN A GASEOUS OR LIQUID ENVIRONMENT

PRIORITY

The present application claims priority to U.S. filed provisional patent application U.S. 60/750,729 filed Dec. 15, 2005.

FIELD

The present invention relates to the field of sensors. More specifically, the present invention is directed to a method and a system for measuring physical parameters or detecting the presence of biological or chemical species, in a gaseous or liquid environment.

BACKGROUND

Vibrations of a cantilever without damping are described by D. Landau and E. M. Lifshitz (*Theory of Elasticity*, 3$^{rd}$ ed., vol. 7. Oxford: Butterworth-Heinemann, 1986).

Micro-machined cantilevers are excellent sensors as they are extremely sensitive and miniature, mass produced. and low cost. They operate by detecting changes either in resonant frequency, amplitude, Q-factor or in deflection caused by mass loading, surface stress variation, or any other changes of the cantilever's environment.

Sensors for measuring physical parameters with a vibrating element are known (WO2005043126, Rasmussen et al in Ultramicroscopy 97, 2003 371-376), for example, such sensors may measure pressure. In these devices, a physical parameter is measured without compensation for changes in other parameters in the environment, such as temperature.

As these sensors often show a temperature dependency, various solutions to compensate the output of the sensor for temperature variations have been proposed (EP 0 371 592 B1, U.S. Pat. No. 4,554,927, U.S. Pat. No. 5,379,639, U.S. Pat. No. 5,458,000, U.S. Pat. No. 5,511,427). These patents use two different (vibrating) means to measure pressure and temperature.

For measuring both temperature and pressure, J. Mertens et al (Ultramicroscopy 97, 2003, 119-126) and R. Sandberg et al (J. Micromech. Microeng. 15, 2005, 1454-1458) proposed one single microcantilever. In both cases a piezoelectric transducer actuates the cantilever. Resonant frequencies were determined by cantilever deflection measurements from the deflection of a laser beam reflecting off the cantilever top surface. Extra optical means are required for measuring the cantilever deflection by this method, and it is not straightforward.

Also known in the field is the use of piezoelectric materials, both for electrical actuation and electrical sensing. Here, a change in the resonance frequency allows defining a change in a parameter, such as a change in viscosity of the surrounding medium, or a change in mass load of the cantilever (WO2005/043126).

U.S. Pat. No. 4,144,747 and Zheyao Wang et al in Meas. Sci. Technol. 11, 1565-1569 (2000) mention the use of two resonant modes of a quartz resonator to measure a force, thereby compensating for the temperature.

However, there is a need to measure more than one parameter using only one piezoelectric bimorph cantilever in a gaseous or liquid environment so as to compensate for changes in other parameters. It is also desirable to make such a sensor very small and highly sensitive.

SUMMARY

An example method and structure for measuring at least two physical parameters in a gas or liquid environment is described. (e.g., temperature, pressure, weight, and concentration of chemical and biological species).

One example method includes providing a piezoelectric bimorph cantilever comprising at least a first layer, a piezoelectric layer, and two electrodes; placing the bimorph cantilever in the gas or liquid environment; vibrating the bimorph cantilever; determining the resonant frequency of at least two resonance modes of the bimorph cantilever; and determining at least two physical parameters of the environment based on the two resonance modes.

An example sensor structure may include a bimorph cantilever having a first layer, a piezoelectric layer, and two electrodes; a support on which the bimorph cantilever is mounted; electrical connections to the electrodes of the bimorph cantilever; means for vibrating the bimorph cantilever with the electrodes; means for measuring an output signal of the electrodes; means for determining the resonant frequency of at least two resonance modes based on the output signal of the electrodes; means for determining at least two physical parameters of the environment based on the resonance frequencies; and optionally, a protective housing.

As an example, the first layer of the bimorph cantilever may include materials such as silicon (Si), silicon nitride (SiN), silicon carbide (SiC), diamond, and silicon oxide (SiO$_2$). The piezoelectric layer may include materials such as Lead Zirconate Titanate (PZT), zinc oxide (ZnO), aluminum nitride (AlN), and barium titanium oxide (BaTiO$_3$). And, the electrodes may include materials such as gold (Au), aluminum (Al), platinum (Pt), and titanium nitride (TiN). In addition, an adhesion layer (e.g., titanium (Ti)) may be positioned between the electrode material and the first layer or the piezoelectric layer. The bimorph cantilever may also include a layer for binding biological or chemical species.

In an additional example, the piezoelectric bimorph cantilever may be fabricated by a process that includes providing a first layer; depositing a first electrode material on a portion of the base material; depositing a piezoelectric material on a portion of the first layer; depositing a second electrode material on a portion of the piezoelectric material; and patterning the first layer and the piezoelectric material in a cantilever shape. Furthermore, the bimorph cantilever may be coated with a layer that allows biological or chemical species to bind to the cantilever.

The electrodes of the bimorph cantilever may be coupled to an analysis tool or an electronic network. To do this, the cantilever may be mounted on a support and optionally include a housing.

The bimorph cantilever may be vibrated by applying an AC voltage across the cantilever's electrodes. Determining the resonant frequency of the two resonance modes of the bimorph cantilever may be achieved with an impedance analyzer, for example.

The resonant frequency of the bimorph cantilever may be determined using a frequency-selective network. In addition, the frequency-selective network may also be mounted on a support comprising the cantilever.

The at least two physical parameters of the gas or liquid environment may be determined by comparing the two resonance modes with calibration curves. Such comparing may be carried out with integrating electronics on a support that includes the bimorph cantilever.

Particular and preferred aspects of the invention can be found in the independent and dependent claims. Features from the dependent claims may be combined with features of the independent claims and with features of other dependent claims.

The characteristics, features, and advantages of the invention will be clarified in the detailed description in combination with the drawings, which illustrate the principles of the invention. This description is given as an example only, without limiting the scope of the invention.

DETAILED DESCRIPTION

Figure 1:
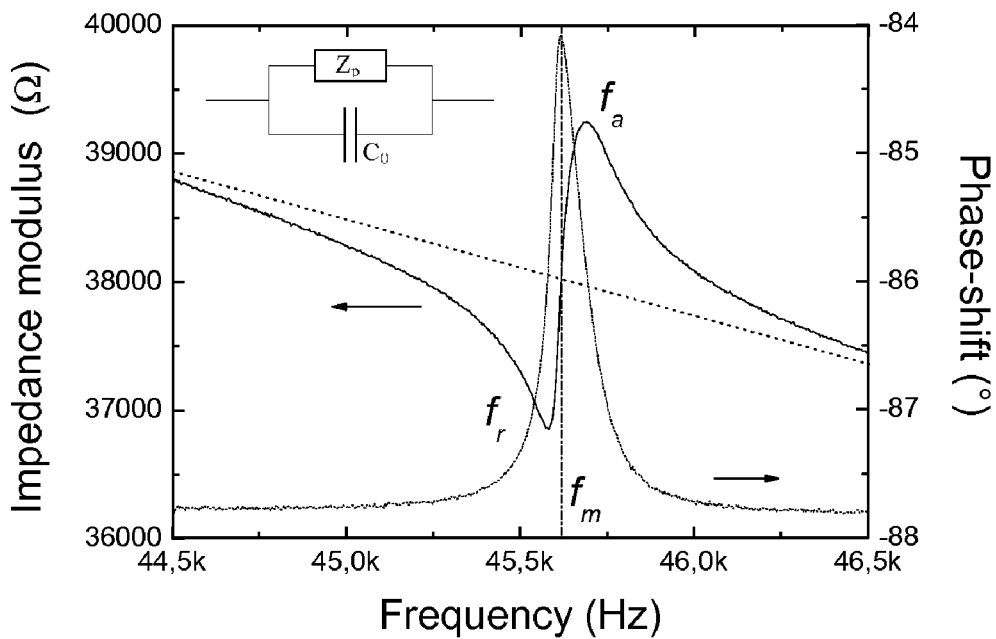
FIG. 1 shows the experimental impedance modulus and phase-shift of a piezoelectric bimorph cantilever as a function of the frequency. In the inset, the electric equivalent circuit of the piezoelectric bimorph cantilever is presented.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like both in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The present invention relates to the field of sensors, where the parameters to be sensed affect the resonant frequencies of a vibrating element (i.e., a piezoelectric bimorph cantilever). Disclosed herein are a measurement method and a system, and a sensor for measuring physical parameters in a gaseous or liquid environment, such as temperature, pressure, or sensing biological or chemical species. Described are the various components needed to operate the sensor, various methods to vibrate the cantilever, and how to determine physical parameters. Also disclosed is a method for producing the piezoelectric bimorph cantilever and the piezoelectric bimorph cantilevers.

The sensor comprises a piezoelectric bimorph cantilever (for placing in a gas or liquid), means for vibrating the cantilever, means for defining the resonant frequencies of this cantilever, and means for correlating the resonant frequencies with the physical parameters. In one example, the sensor may comprise a piezoelectric bimorph cantilever including two electrodes mounted on a support, eventually in a protective housing; electrical connections to electrodes of the bimorph cantilever; means to actuate the bimorph cantilever; means for measuring the resonant frequencies of at least two resonance modes; and means for using the measured resonant frequencies for determining physical parameters of the gas or liquid or the presence of chemical and biological species.

The piezoelectric material of a bimorph cantilever sensor allows for direct electrical measurement of the resonance frequencies, making the piezoelectric material useful for both actuation and detection. Consequently, piezoelectric detection and actuation can be done simultaneously, which makes the sensor smaller and simpler than optical detection (J. Mertens et al. in Ultramicroscopy 97, 2003, 119-126 and R. Sandberg et al. in J. Micromech. Microeng. 15, 2005, 1454-1458) because no extra means for detecting cantilever movements are needed. Thus, the described method and sensor use the piezoelectric thin film of the bimorph cantilever to achieve both actuation and measurement of resonant frequencies. Also, the feature of being very small allows the bimorph cantilever to take up less space in measurement equipment. Furthermore, a cantilever may be designed so that it is very sensitive to changes in parameters in the surrounding gas or liquid atmosphere (e.g., pressure or temperature, or changes in mass load of the cantilever).

In addition to the direct electrical excitation and detection of resonant frequencies, the bimorph cantilever can measure both the pressure and the temperature simultaneously of a known gas without the need of a reference pressure. In contrast to membrane deformation techniques, which run the risk of membrane breakage, the bimorph cantilever does not employ such differential measurement methods, (D. Cullen and T. Reeder "Measurement of SAW velocity versus strain for YX and ST quartz" in Proc. Ultrasonics Symposium 1975 p. 519-522).

In one method, a vibrating bimorph cantilever may measure the resonant frequency of one or more resonance modes. When physical parameters or the composition of the surrounding atmosphere of the bimorph cantilever change, the mechanical resonant frequencies at different frequency modes likewise change. The change in mechanical resonant frequencies may also be induced by a change in the cantilever mass. For example, the cantilever mass may change when material is adsorbed on the cantilever surface. This may occur when the relative humidity in the surrounding atmosphere changes or when biological or chemical species adsorb on the cantilever surface. To selectively adsorb certain biological or chemical species, the cantilever may be coated with specific layers suited for adsorption of a selected material.

Physical parameters or the composition of the gaseous or liquid environment can be determined by basing them on these resonant frequencies. Combining the resonance frequencies of at least two resonance modes allows at least two physical parameters to be determined. Alternatively, it may allow for the measuring of one or more parameters, thereby compensating for other parameters.

In a gas, changes in temperature or pressure can be measured. Also, at a constant temperature and pressure, the sensor can detect a variation of a gas composition. This may be done if the gas consists of only one or two different elements. Using more than one resonance mode, the composition can be defined in combination with temperature or pressure. It is also possible to define the nature of the gas in which the piezoelectric cantilever is located. Besides gas composition, humidity can be measured by changes in the mass load of the cantilever. By coating the cantilever with a gas adsorbing layer, such as gamma-Aluminum (see U.S. Pat. No. 6,531,099), the sensitivity can be increased. In addition, the presence of certain chemical of biological species can be obtained by coating the cantilever with a layer sensitive to a desired species. When the desired chemical or biological species are present, this will cause a change in mass load and, consequently, a change in resonance frequency.

In a liquid, the temperature and density of the liquid can be measured. Also, the presence of certain chemical of biological species in the liquid can be obtained. Coating the cantilever with a layer sensitive to a desired species increases the sensitivity for defining the presence and even concentration of the desired species. When the desired species are present, this will cause a change in mass load and, consequently, a change in resonance frequency.

Because the sensor and its method of operation are closely related, both aspects will be described together. For the same reason, the piezoelectric bimorph cantilever and its method of fabrication will also be described together.

The experimental impedance modulus and phase-shift of a piezoelectric bimorph cantilever (see FIG. 2) is plotted as a function of frequency in FIG. 1. Mechanical resonant frequencies can be found at different frequency modes (peak in FIG. 1). The corresponding impedance (both amplitude and phase) show peaks near these resonant frequencies (see FIG. 1). The inset of FIG. 1 shows the equivalent circuit of a piezoelectric bimorph cantilever (see FIG. 2) without damping. The equivalent circuit consist of a static capacitance $C_0$ in parallel with a motional impedance $Z_p$, which is a function of the substrate and piezoelectric material properties and cantilever dimensions. Near the mechanical resonance, the motional impedance is non-zero and the impedance of the cantilever differs from the impedance of the static capacitance. The mechanical resonant frequency of the cantilever ($f_m$) is located at the maximum of the phase-shift where the motional impedance equals zero. The local minimum and maximum of the impedance correspond to the electrical resonant ($f_r$) and anti-resonant frequencies ($f_a$), respectively.

When the bimorph cantilever is introduced in a surrounding gas or liquid atmosphere, it becomes a damped cantilever. The vibration of this cantilever can be influenced by the nature and the physical parameters of the surrounding atmosphere. Also a change of the mass of the cantilever caused by adsorption, condensation or binding of specific molecules, influences the vibration of the cantilever.

Figure 3:
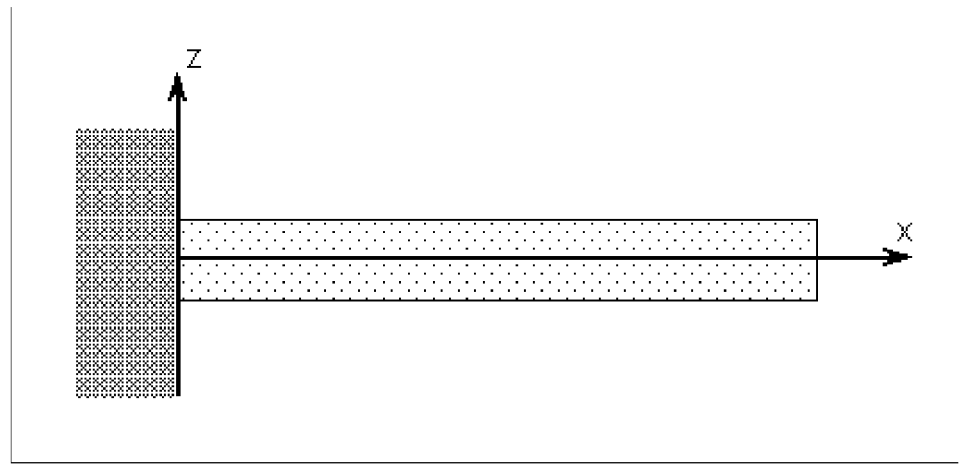
FIG. 3 shows a simple cantilever with Young's modulus E.

The equation of motion describing the dynamic operation of a simple (not bimorph) damped and driven cantilever (see FIG. 3) is as follow:

$$EI_y \frac{\partial^4 X}{\partial z^4} + \chi \frac{\partial X}{\partial t} + \rho S \frac{\partial^2 X}{\partial t^2} = F_0 \sin(\omega \cdot t) \quad (1)$$

where $X(z, t)$ is the deflection of the cantilever at the point z and the time t. The z axis is along the axis of the cantilever. E is the Young's modulus, $I_y$ is the moment of inertia, $\chi$ is the damping coefficient, $\rho$ the mass/unit area of the cantilever, S the cross-section surface, and $F_0$ is the intensity of the harmonic driving force. If we consider that the solutions have the form: $X(z,t)=X_0(z)\cdot T(t)$ with $T(t)=A\cdot\exp(j\omega t)$, equation (1) becomes:

$$\frac{d^4 X_0}{dz^4} + \frac{j\omega\chi}{EI} X_0 - k^4 X_0 = 0 \quad (2)$$

$$\frac{d^2 T}{dt^2} + 2\lambda \frac{dT}{dt} + \omega_0^2 T = F_0 \cdot \sin(\omega \cdot t) \quad (3)$$

where $2\lambda=\chi/\rho S$, $k^4=\omega_o^2 \rho S/EI_y$. If we consider $j\omega\chi/EI_y$ negligible, the solutions $X_0(z)$ of the damped cantilever are the solutions of the un-damped cantilever $X(z)$ [1,2]. Thus the solution X(z,t) of the damped cantilever are the solution X(z) of the un-damped cantilever combine with the solutions of the damped oscillator T(t):

$$T(t) = A(\omega) \cdot e^{j(\omega \cdot t - \varphi)}$$

with $$A(\omega) = \frac{F_0}{\rho S} \frac{1}{\sqrt{(\omega_0^2 - \omega^2)^2 + (2\lambda\omega)^2}}$$

and $$\varphi(\omega) = arctg\left(\frac{2\lambda\omega}{\omega_0^2 - \omega^2}\right)$$

$A(\omega)$ is maximum at $\omega=(\omega_0^2-2\lambda 2)^{1/2}$. For $2\lambda^2/\omega_0^2<1$, $\omega \sim \omega_0 - \lambda^2/\omega_0$ and $\omega \sim \omega_0 - \alpha \cdot \lambda$ ($\alpha$ constant) for $\lambda<<1$. Thus, the resonant frequency varies quasi linearly with the damping coefficient.

The current invention uses this behavior to determine different physical parameters (e.g., pressure) of a gaseous or liquid environment surrounding a bimorph cantilever.

The bimorph cantilever can also detect changes in the composition of the surrounding environment either due to a variation of physical properties changing the damping coefficient (e.g. change in gas composition) or due to mass loading by specific binding events on the cantilever (i.e., from chemical or biological species). In the latter case, the bimorph cantilever can be described as an oscillator with a spring constant K, an effective mass $m_i^*$ of the cantilever of resonance mode j, and resonant frequencies:

$$f_{i0} = \frac{1}{2\pi}\sqrt{\frac{K}{m_i^*}}$$

An additional mass, $\Delta m$, due to binding events is related to the shift in frequency from $f_{io}$ to $f_{i1}$ the different modes by:

$$\left(\frac{1}{f_{i1}}\right)^2 - \left(\frac{1}{f_{i0}}\right)^2 = \frac{\Delta m}{4\pi^2 K}$$

Therefore, the bimorph cantilever is mounted in a gas or liquid of which the physical parameters or composition need to be measured.

Various methods can be used to vibrate the piezoelectric bimorph cantilever, to measure the resonant frequencies of the piezoelectric bimorph cantilever, and to determine the related physical parameters of the gas or liquid. Because the change in resonant frequency of a mode varies with different parameters, a parameter may be defined by a distinct resonance mode. For example pressure and temperature can be measured simultaneously using two different resonance modes. Also, mass load caused by the presence of biological species in combination with temperature can be measured simultaneously using two different resonance modes. Furthermore, dimensions of the cantilever and materials can be optimized to achieve better sensitivity.

The electromechanical coupling coefficient ($k^2$) of the piezoelectric bimorph cantilever is given by:

$$k^2 = k_F^2 \cdot F$$

with $$k_F^2 = \frac{e_{31}^2}{C_{11}^E \cdot \varepsilon_{33}^S}$$

where $e_{31}$ is the piezoelectric coefficient of the piezoelectric layer, $\varepsilon_{33}$ the permitivity, and $C_{11}$ the elastic coefficient, and $k_F^2$ the electromechanical coupling factor of a non-symetric bimorph according to the IEEE Standards of piezoelectricity. F is a form factor, which depends on the elastic properties of the bimorph's materials ($Y_s$, Young's modulus of the substrate of the bimorph cantilever) and the cantilever dimensions. The higher the electromechanical coupling coefficient $k^2$, the better electronic signal. Therefore, the electromechanical coupling factor $k_F^2$ and form factor F need to be maximized.

Values of the coefficient $k_F^2$ have been calculated for different piezoelectric and ferroelectrics materials (see Table 1 below). In spite of its high dielectric constant, the most suitable material is Lead Zirconate Titanate (PZT4) due to its high piezoelectric constant $e_{31}$ and its low elastic constant $C_{11}$.

TABLE 1

Properties of piezoelectric/ferroelectric materials and their $k_F^2$ value.

|  | $C_{11}$ (Gpa) | $e_{31}$ (C/m$^2$) | $\varepsilon_{33}$ ($\times 10^{-11}$ F/m) | $k^2_{Fa.u.}$ |
|---|---|---|---|---|
| PZT4 | 139 | −5.2 | 560 | 3.47 |
| BaTiO$_3$ | 275 | −2.65 | 97 | 2.63 |
| ZnO | 210 | −0.57 | 9.03 | 1.71 |
| AlN | 345 | −0.58 | 9.5 | 1.03 |
| GaN | 390 | −0.49 | 11 | 0.56 |
| LiNbO$_3$ | 203 | 0.2 | 25.7 | 0.08 |

Figure 4:
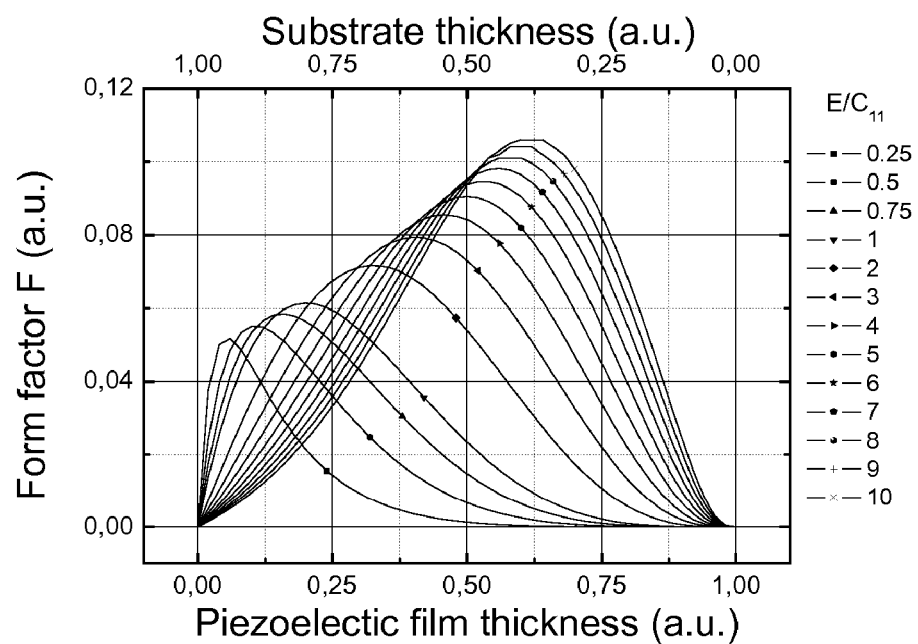
FIG. 4 shows the form factor (F) as a function of the substrate ($h_s$) and the piezoelectric material ($h_c$) thickness at different values of the ratio $Y_s/C_{11}$.

The form factor F is plotted in FIG. 4 as a function of substrate thickness $h_s$ and piezoelectric material thickness $h_c$ for different values of the ratio $\Delta=Y_s/C_{11}$. The form factor has a maximum, being a function of $\Delta$. Thus, using the mechanical properties of the materials that compose the bimorph, an optimized cantilever geometry can be found, i.e. an optimum value for the couple ($h_s$, $h_c$). One can observe that the highest values of the form factor are obtained at the high values of the ratio $\Delta=Y_s/C_{11}$. The stiffer the substrate, the higher the form factor is and, consequently, the higher the electromechanical coupling coefficient.

Based on the calculations and graphs above, a substrate or base layer, or first layer and piezoelectric material(s) can be selected. Accordingly, the optimum dimensions for the cantilever can then be chosen. As mentioned above, the highest values for the form factor can be obtained for substrates having a high Young's modulus.

Different functional layers can be deposited on a base material or substrate, also called first layer (i.e., a first electrode material, a piezoelectric material, and a second electrode material). That way, the cantilever comprises a base material or substrate or first layer, a piezoelectric material and electrodes connected to the piezoelectric material for both actuation and sensing purposes.

The first layer or substrate or base material can be a piezoelectric material or a non-piezoelectric material. Good choices for the substrate material or first layer are materials with a high Young's modulus, such as silicon carbide (SiC) and diamond. Also silicon (Si), silicon nitride (SiN), and silicon oxide ($SiO_2$)) can be used. Diamond, which has a high Young's modulus, is a suitable material for this type of cantilever. In addition, diamond also has advantageous bio-compatibility and stability properties, which are useful for binding biological molecules. For example, diamond may be used to create a biosensor (e.g., for attaching DNA on its surface).

The substrate thickness or thickness of the first layer or base material can be chosen in between 200 nm and 2 µm, with a maximum substrate thickness of 7.5 µm.

The substrate thickness is typically in between 250 nm and 1000 nm.

The piezoelectric material can fully cover the underlying material or can cover only part of the underlying material. This local deposition can be obtained by evaporation through a shadow mask or by using lithography with dry and/or wet etching or lift-off. The piezoelectric material can be deposited by PVD methods (e.g., sputtering, ablation), CVD methods, or hydrothermal method. Good choices for the piezoelectric material are piezoelectric materials with a high $k_F^2$ coefficient such as Lead Zirconate Titanate (PZT), zinc oxide (ZnO), aluminum nitride (AlN), barium titanium oxide ($BaTiO_3$). With regard to piezoelectric coupling properties, Lead Zirkonate Titanate (PZT4) may be preferable (see Table 1). For dry gas sensing, a material having a high piezoelectric coefficient may be chosen. In addition, such a material should not be damaged by water/fluid ab/adsorption. Also, because humidity condensation of water/fluid increases the effective mass of the cantilever, hydrophilic piezoelectric bimorph cantilevers may be employed as dew point sensors The thickness of the piezoelectric material can be chosen between 200 nm and 2 µm, with a maximum thickness of 7.5 µm, depending on the desired frequency of operation and the cantilever length and mechanical stiffness. Higher frequencies often result in a higher sensitivity. The thickness may be on the order of 1-2 µm. Examples of piezoelectric bimorph cantilever dimensions are given by Don L. DeVoe and Albert Pisano in IEEE Journal of Microelectromechanical Systems, Vol. 6, No. 3, September 1997).

The general relationship between the thickness of the cantilever and sensitivity is as follows: the thinner the cantilever, the higher the resonance frequency, and consequently, the higher the sensitivity. Therefore, sensitivity may be maintained or tailored by inuring that the total cantilever thickness is thin. Typical values for the total thickness are in between 200 nm and 2 µm. Good sensitivity may be found total thicknesses that are less than 10 µm.

The electrode materials can fully cover the underlying material or can cover the underlying material only partially, thereby being shaped for a desired use. The electrode materials can be deposited by different techniques known in the art, such as thermal evaporation, e-beam evaporation, physical vapor deposition, sputtering, or chemical vapor deposition. Local deposition can be obtained by evaporation through a shadow mask or by using standard lithography with dry and/or wet etching or lift-off.

The electrode material may comprise gold (Au), aluminium (Al), platinum (Pt), Palladium (Pd), Rhodium (Rh), Ruthenium (Ru), Osmium (Os), Iridium (Ir), titanium nitride (TiN) or doped polysilicon (doped polysilicon because it is used in microelectronics integrated circuits).

To improve adhesion between the electrode material and the piezoelectric material and/or the substrate, intermediate adhesion layers can be used, such as titanium (Ti) or any other material improving the adhesion between the electrode material and the underlying material.

Typically, the thickness of the electrodes is in between 20 nm and 500 nm, preferably in between 100 and 200 nm. The electrodes needs to be thick enough to insure good and reliable electrical contact. On the other hand, the thickness cannot be too thick or else the internal damping effect will be limited.

Shaping the cantilever may be carried out using MEMS processing (Microelectronic Mechanical Systems) techniques or using standard photolithography processes with dry or/and wet etching or lift-off. Fine tuning of the cantilever properties can be carried out with focused ion beam ablation, for example.

For detecting the presence or absence of specific biological or chemical molecules, the cantilever can be coated with a layer specifically binding a desired type of molecules. When such molecules are present, they will bind to the coated layer, thereby inducing a change in the mass of the cantilever. The corresponding change in the resonance frequency indicates the presence of these molecules.

Figure 2:
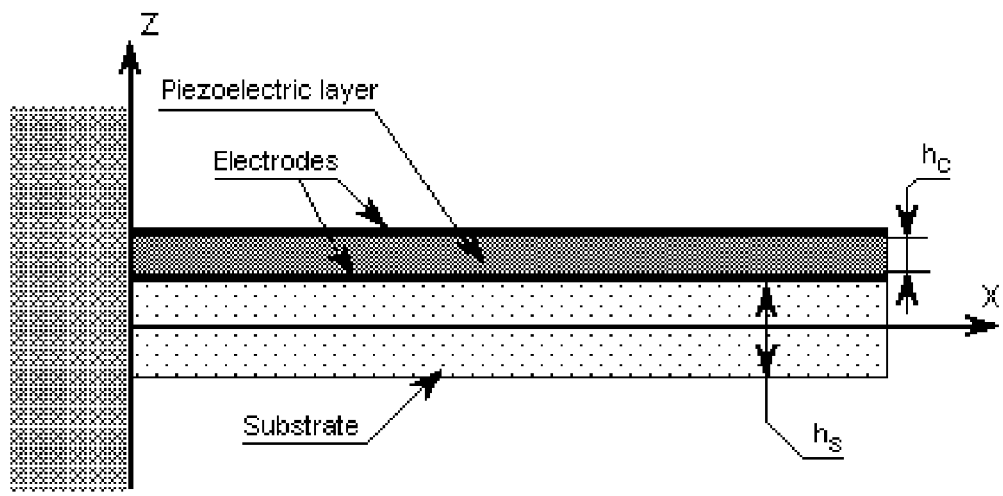
FIG. 2 shows a piezoelectric bimorph cantilever with $Y_s$ the Young modulus of the substrate material, and $C_{11}$, the elastic stiffness coefficient of the piezoelectric material.
Figure 5:
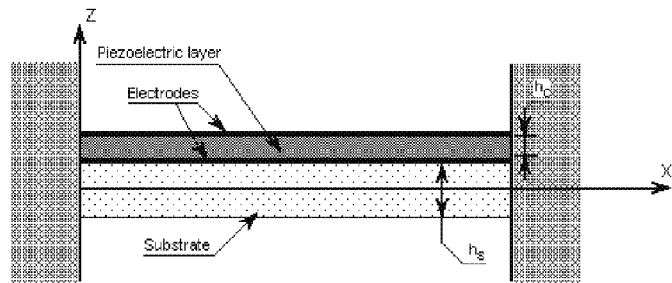
FIG. 5 shows a piezoelectric bimorph cantilever clamped at two sides.

The cantilever can be clamped at one side (see FIG. 2). Also, a clamped cantilever, which is fixed at two sides, can be used (see FIG. 5). Compared to the cantilever represented in FIG. 2, a clamped cantilever may be even more sensitive to changes in certain parameters because the mechanical stress induced by changes in the surrounding atmosphere (e.g., a temperature change) will be higher. The difference between the thermal expansion coefficient between the fixture and the cantilever can be used to induce an extra temperature-dependent mechanical stress on the cantilever, thereby increasing the sensitivity for temperature variations.

Vibrating the piezoelectric bimorph cantilever and measuring the resonant frequencies of the piezoelectric bimorph cantilever are carried out with an impedance analyzer coupled to the electrodes of the piezoelectric bimorph cantilever. An AC voltage is applied across the two electrodes of the piezoelectric bimorph cantilever using this impedance analyser. Also, an additional voltage source can be used, in which case four- or multiple electrode configurations may be required.

The resonant frequency of at least two resonance modes of the bimorph cantilever is determined by using the impedance analyzer to measure impedance over a frequency range near the envisaged resonance modes. The corresponding resonant frequencies can be found using the impedance modulus (see FIG. 1) at the points where the motional impedance is zero, which is at the point where the impedance of the cantilever differs from the impedance of the static capacitance. Also, the phase-shift curve (see FIG. 1) can be used to find resonant frequencies at points where the phase-shift reaches a maximum. Extracting the resonant frequencies can be carried out by connecting the impedance analyzer to a computer containing software for determining resonant frequencies.

Figure 6:
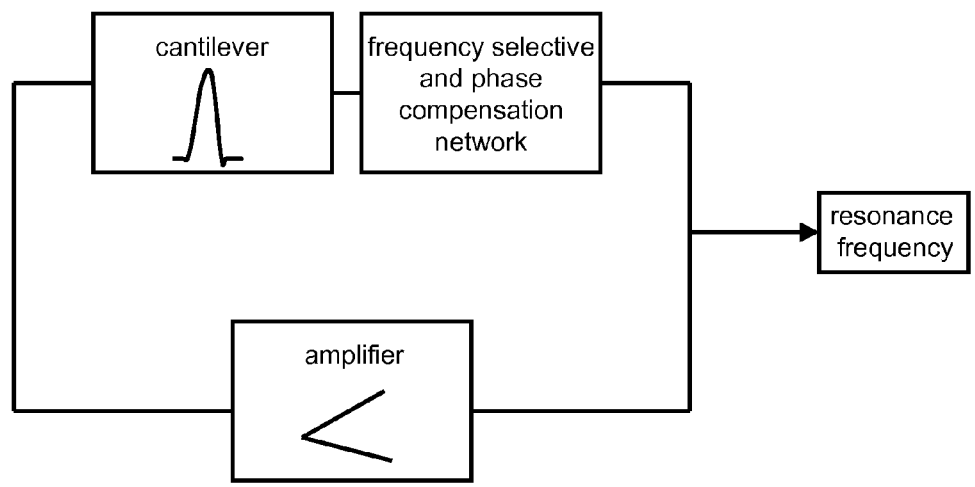
FIG. 6 shows a frequency-selective network that can be used to select one of the resonant modes of the piezoelectric bimorph cantilever and to selectively excite this chosen mode.
Figure 20:
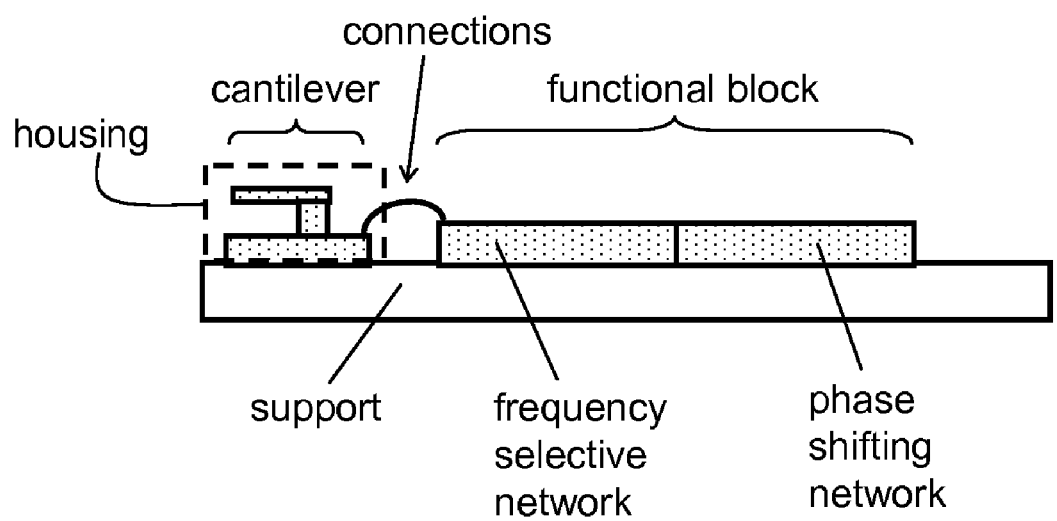
FIG. 20: Cantilever and functional block mounted on a support.

In another approach, the resonance properties of the piezoelectric bimorph cantilever are directly exploited in an oscillator setup (see FIG. 6). In an oscillator setup, the frequency-selective element (i.e., the piezoelectric bimorph cantilever) is placed in the path of a positive feedback loop to an amplifier. In a basic oscillator setup, the strongest mode of oscillation (the fundamental frequency) will be excited. The phase-shift caused by the parasitic capacitances of the cantilever has to be compensated by a phase shifting network. In order to stimulate higher orders of oscillation, a frequency-selective network can be employed in series with the piezoelectric bimorph cantilever. The functions of the frequency-selective network and the phase shifting network can be combined into one functional block. This functional block can be realized using digital signal processing and filtering techniques, which allows a greater flexibility and provides miniaturization possibilities. For example, the functional block can be integrated on the support upon which the piezoelectric bimorph cantilever is mounted along with connections to the electrodes of the piezoelectric bimorph cantilever, as shown in FIG. 20.

Different physical parameters can be determined based on resonant frequencies. For example, determining the resonant frequency of at least two resonance modes allows measuring at least two different parameters. In fact any combination of two or more different parameters can be determined. Often parameters, such as pressure, binding molecules, or any other parameter, need to be measured while compensating for temperature effects. Examples of physical parameters include temperature and pressure. Also, by detecting a change in the resonant frequency, the composition of a gas or a liquid can be determined, as well as a change in the weight of the cantilever. This allows different parameters in a gas or a liquid. As humidity or condensation of water/fluid increases the effective mass of the cantilever, the resonant frequency of the cantilever likewise changes. This allows humidity or condensation to be measured. Hydrophilic piezoelectric bimorph cantilevers may be employed as dew point sensors (which may eventually compensate for the actual temperature). Also, when coating the cantilever with appropriate layers for binding certain biological molecules, the weight of the cantilever will change when these molecules bind to a specific layer. In this manner, the presence or absence of certain biological molecules can be detected by a change in resonance frequency caused by a change in the weight of the cantilever.

The measured resonant frequencies can be compared with calibration curves. These calibration curves can be included in electronics that can be integrated on a support comprising the piezoelectric bimorph cantilever and connections to the electrodes of the piezoelectric bimorph cantilever. It should be understood that there are a multitude of possibilities for integrations. For example, the bimorph cantilever and its hardware implementations may be separated from the calculation/interpretation task, which may be implemented by software adapted to the specific measurement task.

Arrays of cantilevers sensors may also be made, thereby allowing the detection of various parameters or the presence of different biological molecules. Measuring different resonance frequencies allows, for example, compensation for changes in temperature.

EXAMPLE

Described below are experimental results of combined pressure and temperature measurements obtained with a commercially available piezoelectric bimorph cantilever. Both pressure and temperature can be measured simultaneously with a piezoelectric bimorph cantilever using the resonance frequency of two resonance modes.

Figure 7:
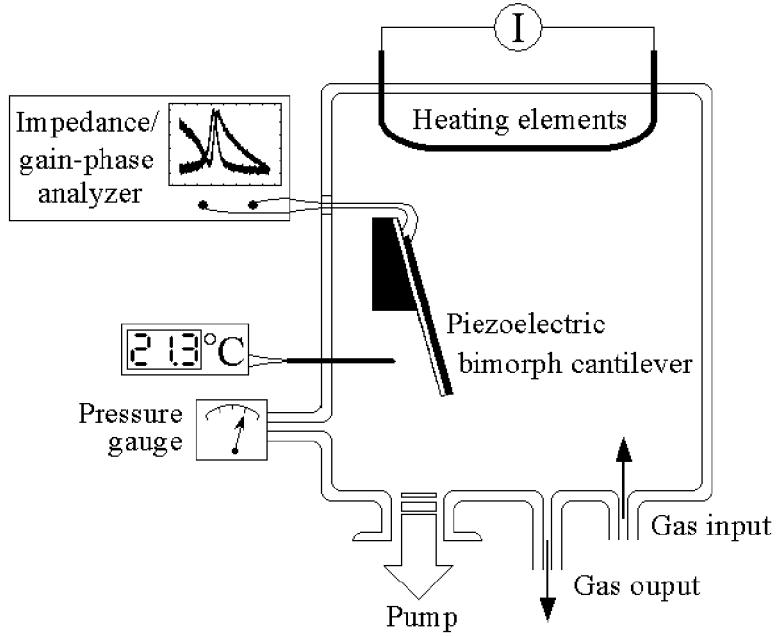
FIG. 7 shows the experimental setup used for determining the temperature and pressure of a gas based on resonance frequencies of a piezoelectric bimorph cantilever.

The experimental set-up is shown in FIG. 7. A commercially available piezoelectric bimorph cantilever, (Veeco©) was used. This cantilever consists of micro-machined silicon with a piezoelectric zinc oxide (ZnO) layer, in combination with two gold (Au) electrodes for vibrating the cantilever. The cantilever was fixed into a gas tight canister and electrically connected to an impedance analyser (HP 4194A) with a BNC cable. The pressure was regulated with a relief valve at the gas inlet and a leaking valve at the gas outlet for high pressures (>1 bar). The pressure was measured with a tire manometer. A pump and a Compact Full Range Gauge (Pfeiffer Vacuum©) were used to control the pressure in the low-pressure range (<1 bar). The pressure could be varied from $10^{-3}$ mbar up to 10 bars. The system was also equipped with a heating element (Thermocoax©) and a type K thermocouple to control the gas temperature. The gas temperature was varied from room temperature up to 80° C. Experiments were carried out with different gases, which included nitrogen, argon and helium.

Figure 8:
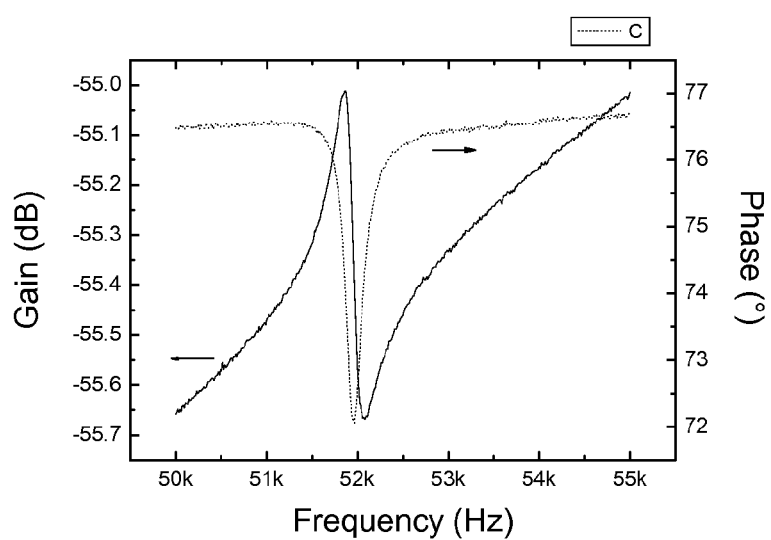
FIG. 8: 1st resonant mode at atmospheric pressure and room temperature of a of Si/ZnO cantilever
Figure 9:
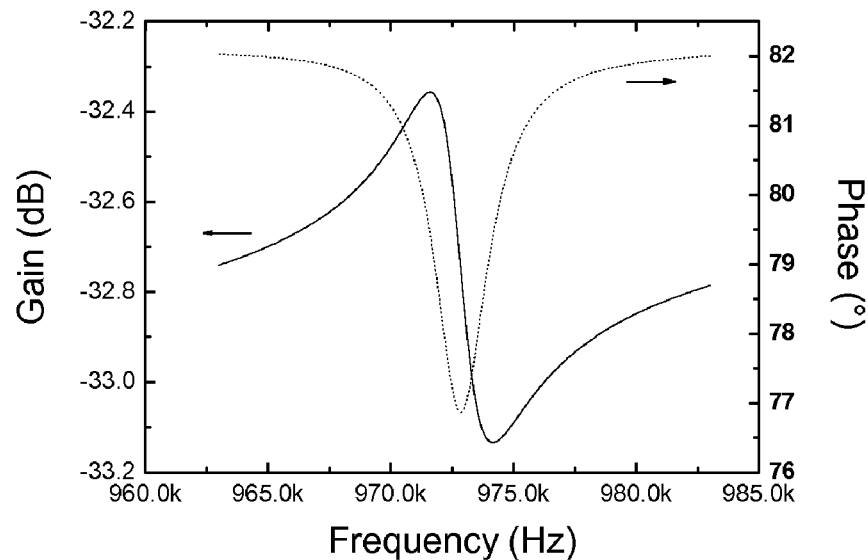
FIG. 9: 3rd resonant mode atmospheric pressure and room temperature of Si/ZnO cantilever.

The electrical properties of the cantilever (Si/ZnO) are represented in FIGS. 8 and 9. FIG. 8 shows the $1^{st}$ resonant mode at atmospheric pressure and room temperature and FIG. 9 shows the $3^{rd}$ resonant mode atmospheric pressure and room temperature of Si/ZnO cantilever.

Figure 10:
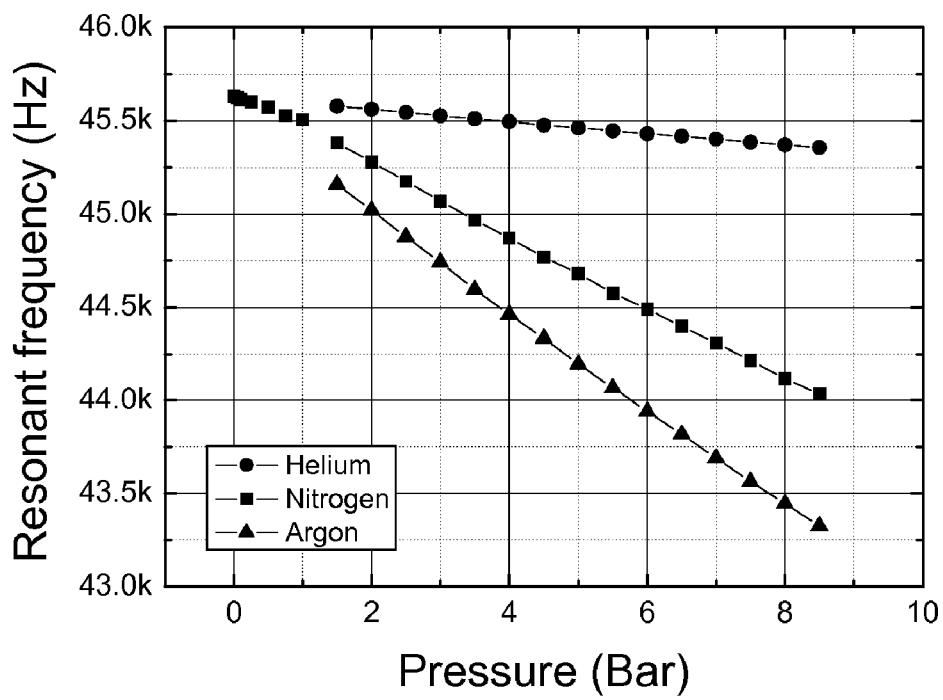
FIG. 10 shows the variation of the resonant frequency as a function of the gas pressure and the nature of the gas for nitrogen, argon, helium.

The cantilever has several resonant modes. The resonant modes, that were used are mode A at 45.555 kHz and mode B at 934.140 kHz. The variation of mode A as a function of the pressure for different gases and at room temperature is presented in FIG. 10. The resonant frequency exhibits a linear behaviour as function of pressure for all gases. However, the sensitivity varies with the gases: 4.22 ppm/mbar for nitrogen, 5.752 ppm/mbar for argon and 0.69 ppm/mbar for helium. Mode B exhibits the same linear behavior with different sensitivities: 3.37 ppm/mbar for nitrogen, 4.53 ppm/mbar for argon and 0.64 ppm/mbar for helium. G. Y. Chen et al in Rev. Sci. Instrum., vol. 65, pp 2532-2537, 1994 indicate that the variations of the sensitivity with the nature of the gas and the vibration modes may be due to:

the variation of the drag force, which is a function of the viscosity and the density of the gas, and the variation of the velocity of the moving object, which is a function of the vibration mode.

Figure 11:
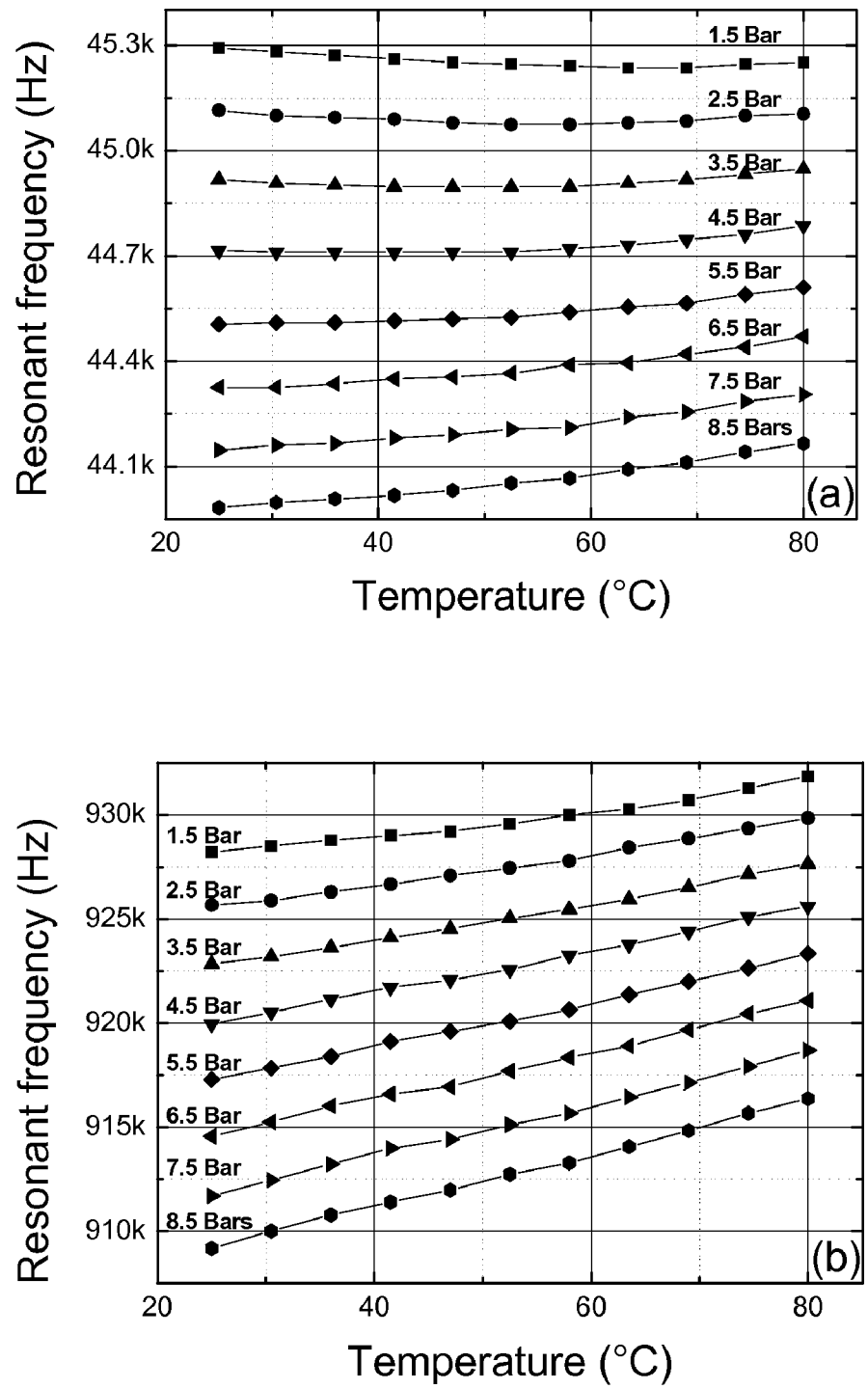
In FIG. 11 the variation of the resonant frequency of (a) mode A and (b) mode B as a function of temperature at different nitrogen pressures is presented.

FIG. 11 shows the variation of the resonant frequency of mode A and mode B as a function of temperature at different nitrogen pressures. The resonant frequency varies quasi-linearly with temperature for both resonant modes. The temperature coefficients of frequency (TCF) of the two modes are different and they slowly increase with the pressure. The TCF increases from ~0 to 75 ppm/K for the mode A and from 68 to 141 ppm/K for the mode B between 1.5 bar and 8.5 bar.

Figure 12:
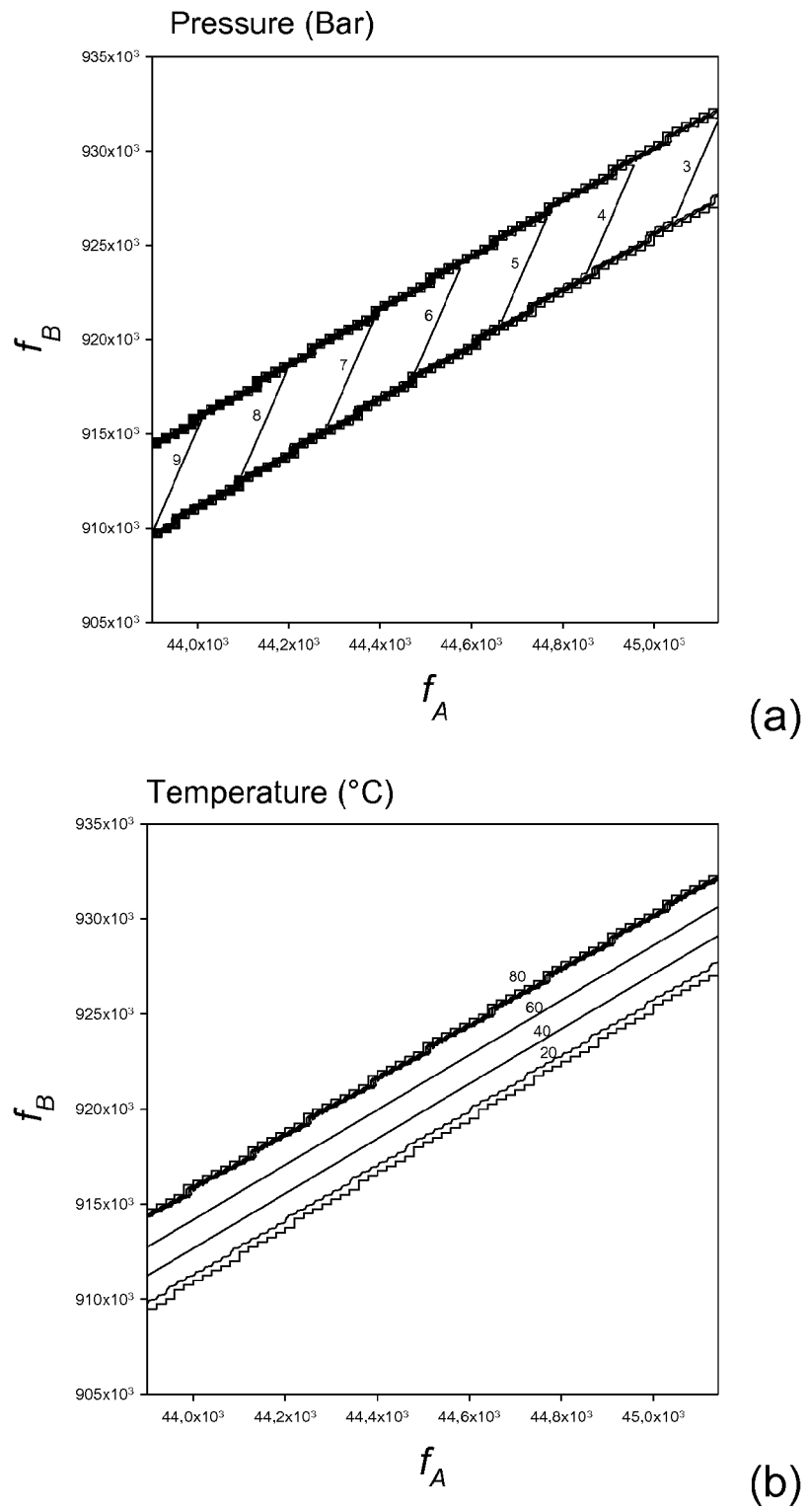
FIG. 12 shows (a) the pressure and (b) temperature plots as a function of the resonant frequencies of the mode A ($f_A$) and mode B ($f_B$).

These results show that the different modes of vibration of a micro-cantilever have different sensitivities to pressure and temperature. For a given pressure and a given temperature, only one couple of corresponding resonant frequencies ($f_A$, $f_B$) is found. That way, both the pressure and the temperature of a known gas can be determined by the monitoring of the resonant frequency of two resonant modes. In FIG. 12, the relationship between pressure, temperature, and resonant frequencies is presented. Using the graphs in FIG. 12 and the two resonant frequencies of mode A and mode B allows pressure and temperature to be determined, eventually using an electronic read-out. Using this experimental set-up both pressure and temperature of a known gas for a pressure up to 10 bars and a temperature between RT and 80° C. was measured. It should be noted that this sensor can operate at higher pressures and higher/lower temperatures.

EXAMPLE

A piezoelectric bimorph cantilever was made by combining a Si substrate coated with diamond. Diamond can be used for binding biological molecules, thereby creating a biosensor. Diamond is bio-compatible, stable, and can be prepared to attach DNA on its surface, for example. Process steps for creating a cantilever are presented in FIGS. 13A-V.

A silicon(100) substrate 1 (see FIG. 13A) is selected for wet chemical etching (anisotropic) in KOH. (i.e (111) surfaces are not etched, (100) has a ~54 degree slant and (110) is a vertical profile). (described with more detail with regard to etching the back-side, see below).

Figure 15:
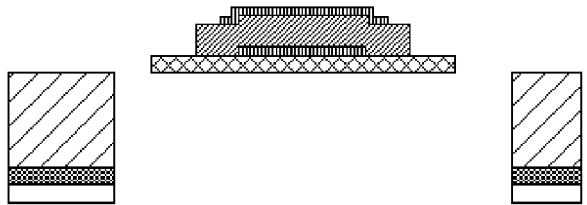
FIG. 15: (a) Front view and (b) side view of piezoelectric bimorph cantilever.
Figure 15:
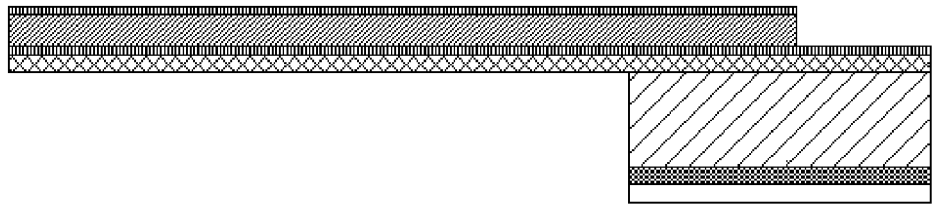

First, a mask was deposited and patterned at the back-side of the sample. Alignment marks may be used to insure that when the Si is etched underneath the cantilever, the cantilever anchorage is at the edge of the Si hole (see FIG. 15). The mask can be either Si3N4 for wet chemical etching (KOH) or Al or photoresist for deep reactive ion etching. In this case Si3N4/SiO2 with wet KOH etch was used. Therefore Si3N4 2 is deposited on the substrate 1 (see FIG. 13B), followed by SiO2 3 deposition (see FIG. 13C). Lithography 4 defined the locations where the Si should be etched (see FIG. 13D). SiO2 was first etched in HF at room temperature (see FIG. 13E) and Si3N4 was etched in H3PO4 at 140° C. (see FIG. 13F). The combined SiO2/Si3N4 layer was used as a hardmask for etching Si in KOH (see FIG. 13T).

Then, nano-crystalline diamond films 5 were deposited on the (100) silicon surface (15×15 mm$^2$) (see FIG. 13G) using microwave plasma enhanced chemical vapor deposition in an Aixtron P6 deposition system. The substrates were bias enhanced nucleated (BEN) to achieve a high nucleation density ($10^{10}$-$10^{11}$ cm$^{-2}$) and to obtain a quickly closed film. A bias voltage of −180 V with 5% of methane in hydrogen and a total pressure of 20 mbar was applied for 12 minutes during the nucleation step. The diamond films were grown in 0.5% of methane in hydrogen, with a total pressure of 20-40 mbar and a microwave power of 900 Watt for 2-3 hours. The diamond films had a thickness of ~0.6-0.7 μm, with a root mean square roughness of 15-20 nm and grain size in the range of 30-100 nm. Nano-diamond is a polycrystalline diamond film with a grain size in the nanometre range, i.e. <1 μm, more generally between 10 to 250 nm. Nanodiamond has the advantage that it has similar properties of polycrystalline diamond without the high roughness which is detrimental to the processing of the cantilever: fine lithography, good crystalline orientation of the piezoelectric material.

Consequently a Cr layer 6 of ~50 nm was deposited (see FIG. 13H), followed by lithography (see FIG. 13I) and wet chemical etching of the Cr (see FIG. 13J) to pattern the bottom electrode. During lithography, the mask is aligned with the alignment marks on the backside of the sample to insure the good location, i.e. the good anchorage of the cantilever when the cantilever will be released by Si eteching. The Cr electrode can also be patterned using lift-off techniques.

Figure 13:
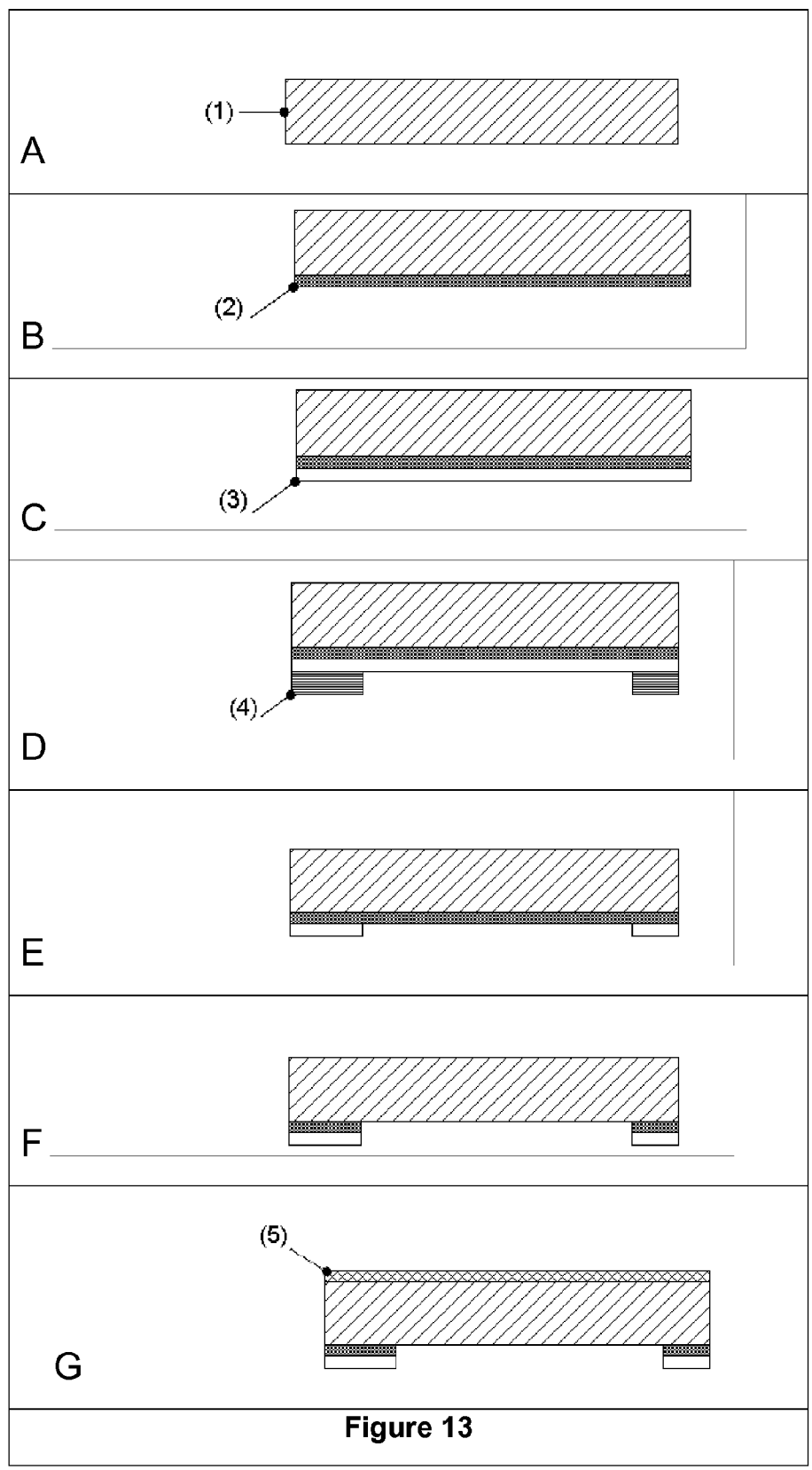
FIGS. 13A-V: Process steps in the fabrication of a bimorph piezoelectric cantilever.
Figure 13:
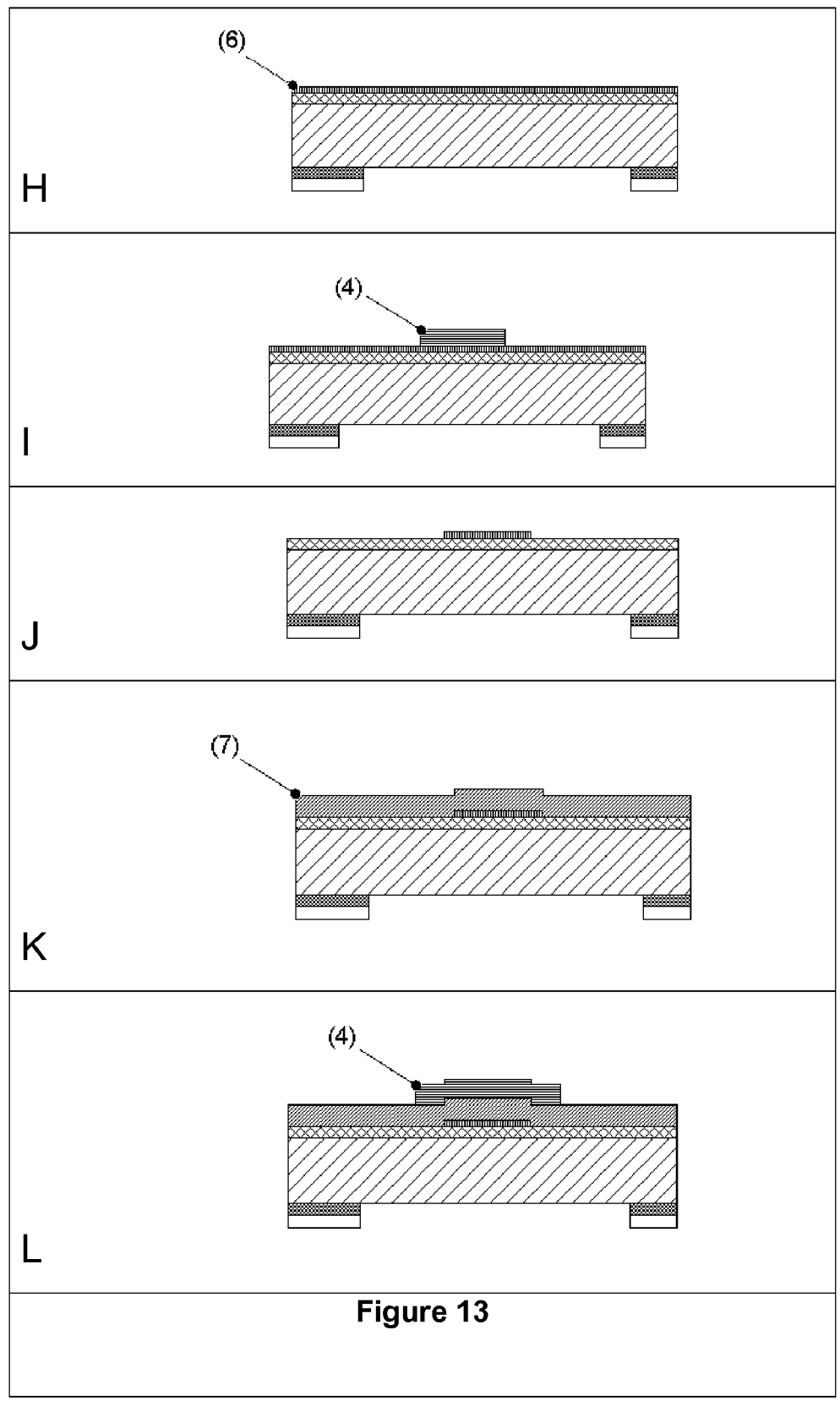
Figure 13:
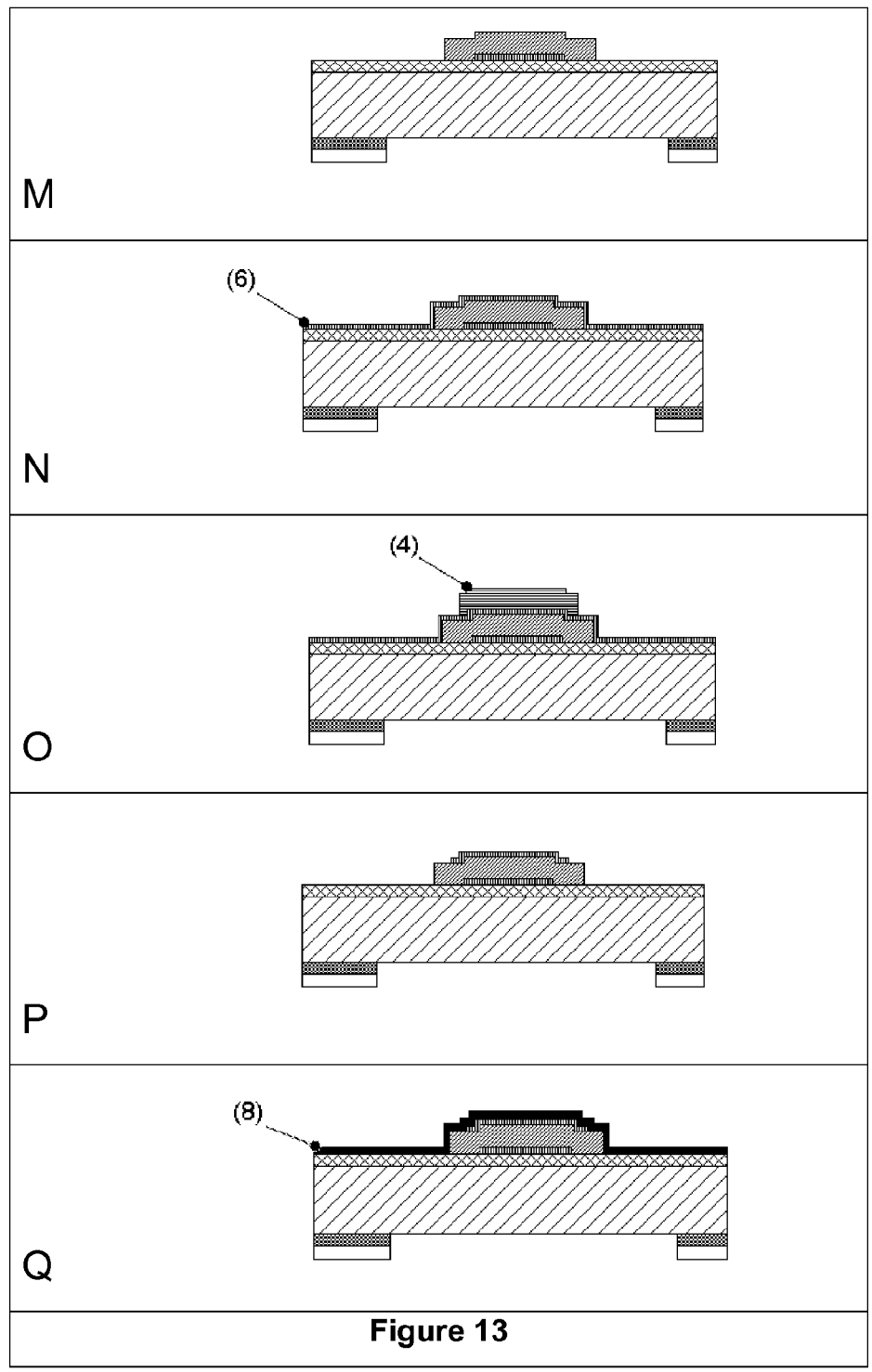
Figure 13:
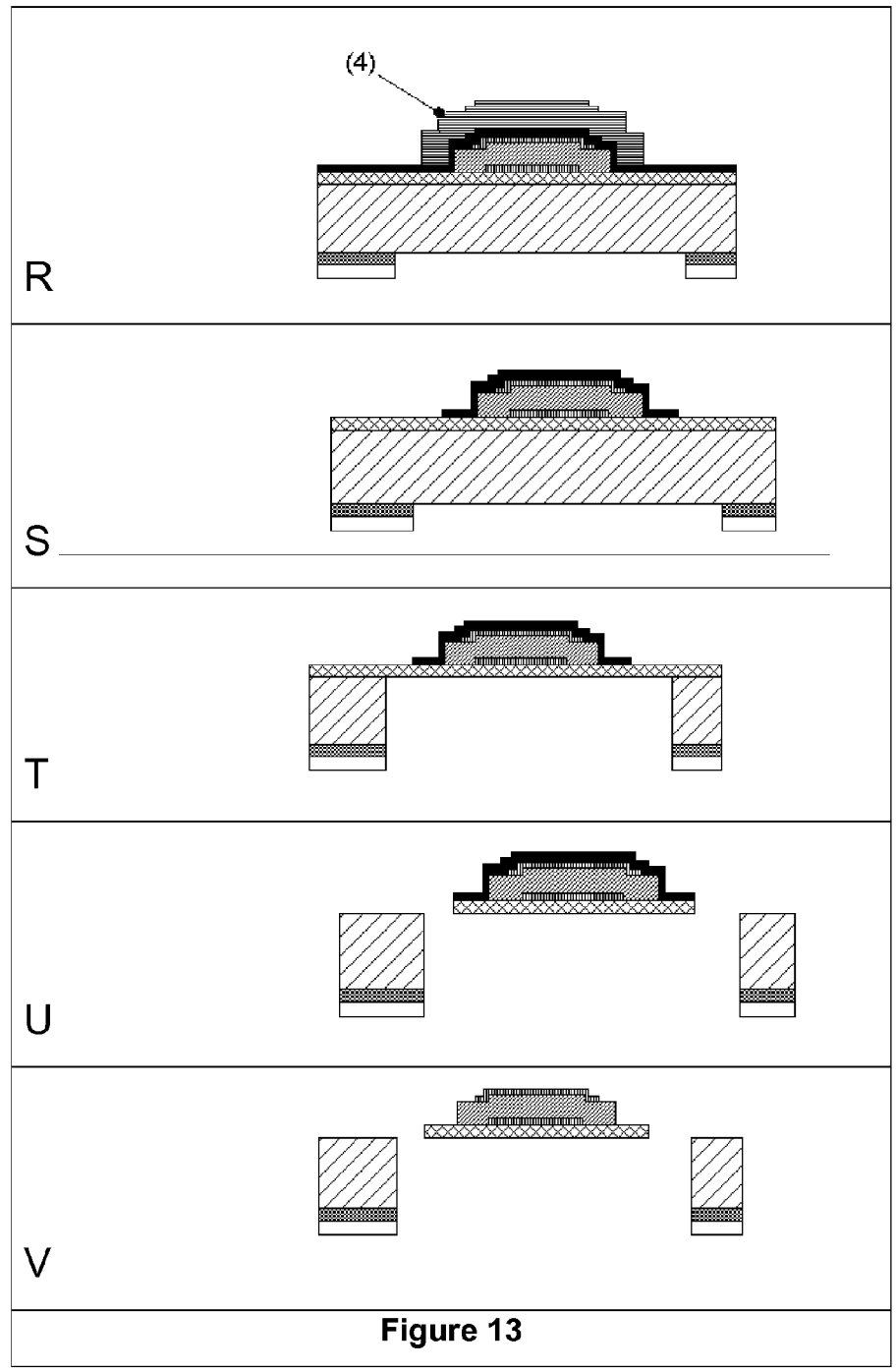
Figure 14:
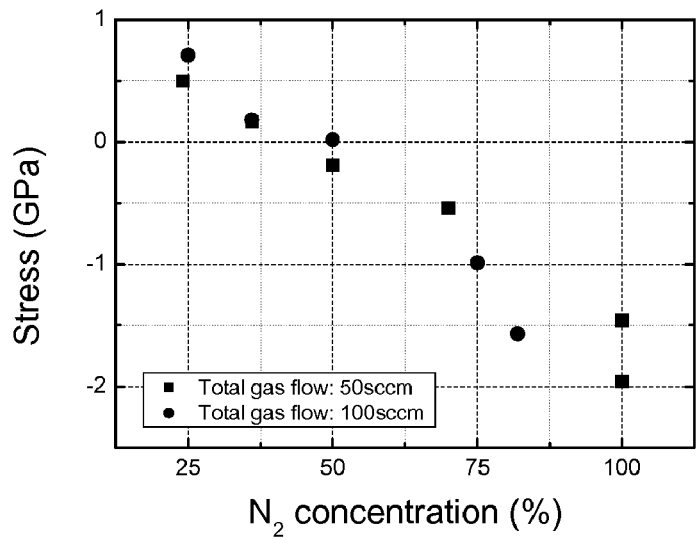
FIG. 14: Variation of the mechanical stress in AlN films as a function of the nitrogen concentration in the gas discharge.

On top of the patterned bottom electrode and the diamond layer, a piezoelectric aluminum nitride (AlN) film 7 of ~1 μm was deposited by magnetron sputtering (see FIG. 13K). The nitrogen concentration $\Phi_N(\Phi_{Ar}+\Phi_N)$, where $\Phi_{Ar}$, $\Phi_N$ are the Argon and Nitrogen flow rates, was optimized to minimize the stress of the AlN layer. The stress varies rather linearly from tensile to compressive as the nitrogen ratio increases and it passes through zero at a nitrogen concentration ~50% (see FIG. 14). AlN was patterned using lithography 4 (see FIG. 13L) and wet chemical etching (see FIG. 13M) in hot H3PO4 (120° C.). Cr has been chosen for the electrodes due to its inertness towards hot H3PO4 (120° C.).

Then a Cr layer of 50 to 100 nm was deposited on top of the AlN 6 (see FIG. 13N) followed by lithography 4 (see FIG. 13O) and wet chemical etching of the Cr to pattern the top electrode (see FIG. 13P).

The diamond/AlN cantilever with Cr electrodes should be isolated from the Si substrate. Therefore diamond at both sides of the cantilever needed to be removed as well as the Si at the bottom.

On top of the stacked layers, Al 8 was deposited (see FIG. 13Q) and patterned by lithography 4 (see FIG. 13R) and dry etch (see FIG. 13S). That way, an Al mask was formed for etching diamond at the edges (see FIG. 13U).

Next, the Si substrate was etched from the back-side with wet anisotropic etching with KOH (see FIG. 13T), which stopped on the diamond layer. (i.e., the diamond layer is acting as a etch stop). The structure on the top-side has to be protected from etching because AlN is etched by KOH. To protect the top-side, the top structure is covered with Apiezon® Wax.

Then, the diamond on top was etched from the top, using the Al layer as mask (see FIG. 13U), with diamond reactive ion etching in oxygen plasma (O2 plasma). Last, the Al mask is removed by chemical etching (see FIG. 13V) and a diamond/AlN cantilever with Cr electrodes was obtained (see FIG. 15). The cantilever was 320 μm long, 70 μm wide, its diamond layer is 0.6-0.7 μm thick, its AlN layer is 1 μm thick and the Cr electrodes are 100 nm thick.

To measure the pressure sensitivity, the cantilever was fixed into a gas tight enclosure and it was electrically connected to an impedance analyzer (HP 4194A) with a BNC cable. The pressure in the canister was regulated with a relief valve at the gas inlet and a leaking valve at the gas outlet. The pressure was measured with a tire manometer. The pressure was varied from vacuum up to 7 Bars. Experiments were carried out in pure nitrogen.

Figure 16:
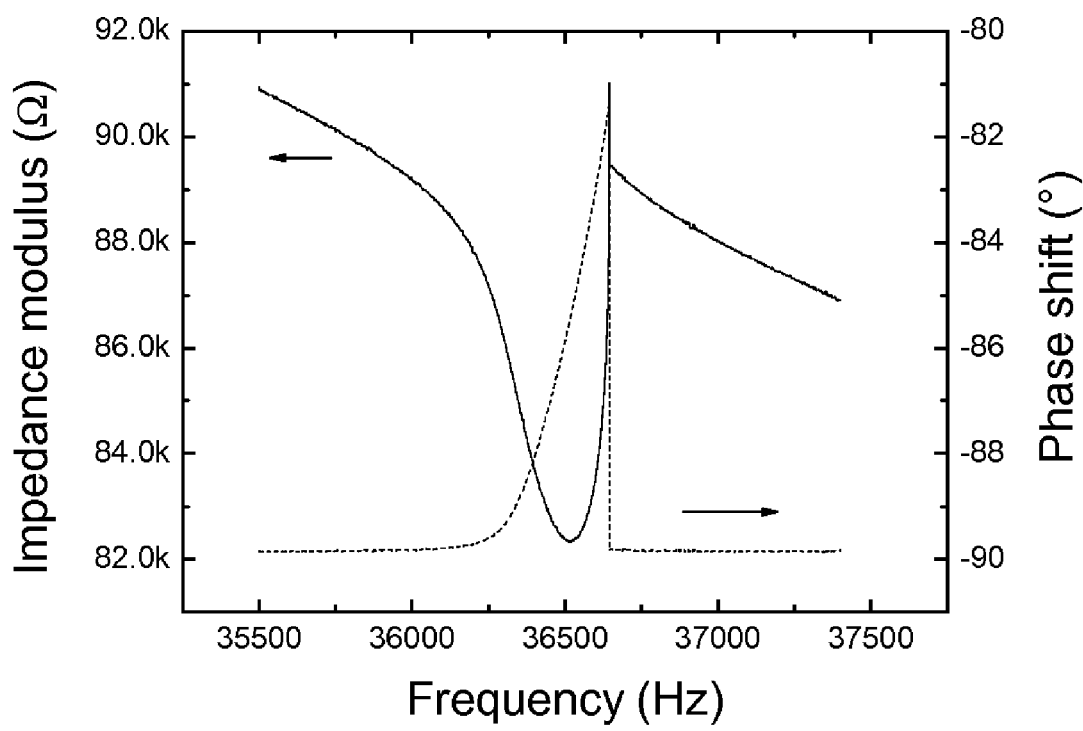
FIG. 16: Variation of the impedance modulus and the phase-shift of diamond/AlN micro-cantilever as a function of the frequency at the first resonant mode. The dashed line represents the static capacitance

First, the different resonant frequencies of the cantilever under vacuum (i.e. without gas damping) were determined. FIG. 16 shows the impedance characteristic plot of the diamond/AlN cantilever at the first resonant mode. The impedance modulus decreases to a minimum, crosses the impedance curve of the static capacitance, increases to a maximum and finally decreases and trends to the static capacitance impedance curve. The mechanical resonance frequency of the cantilever is located at the maximum of the phase-shift and at the crossing with the static capacitive impedance curve. The experimental resonant frequencies values match quite well with the theoretical values obtained using the diamond and AlN properties reported in Table 2.

TABLE 2

Comparison of experimental (under vacuum) and theoretical resonant frequencies of the diamond/AlN micro-cantilever.

| Mode | Experimental frequency (kHz) | Theoretical frequency (kHz) |
|---|---|---|
| 1 | 36.6 | 33.4 |
| 2 | 216 | 209.3 |
| 3 | 588 | 586.0 |
| 4 | 1,109 | 1,149 |
| 5 | 1,643 | 1,899 |
| 6 | 2,831 | 2,836 |

Figure 17:
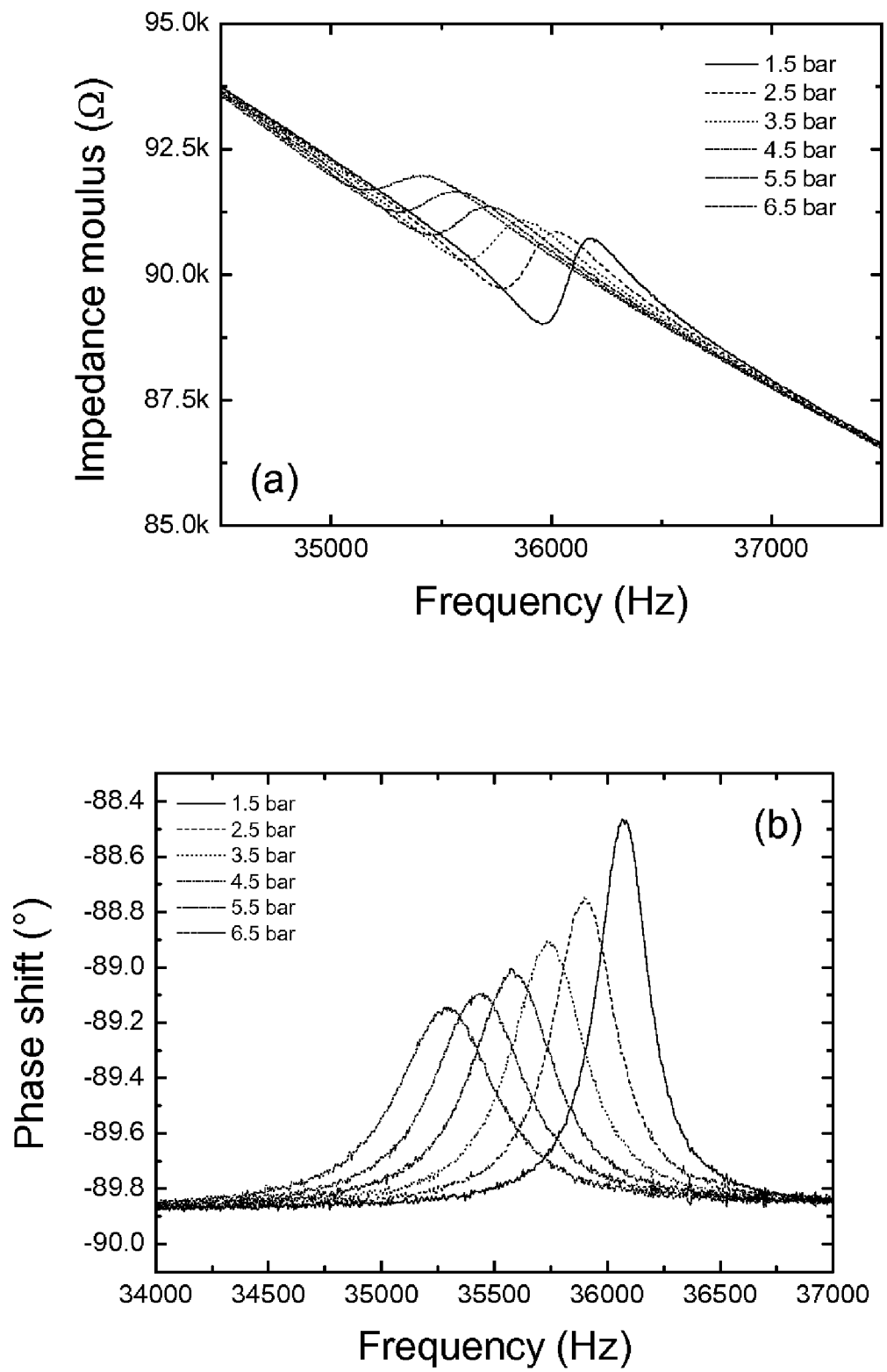
FIG. 17: Variation of the impedance modulus (a) and the phase-shift (b) of diamond/AlN micro-cantilever with frequency at the first resonant mode as a function of nitrogen pressure.
Figure 18:
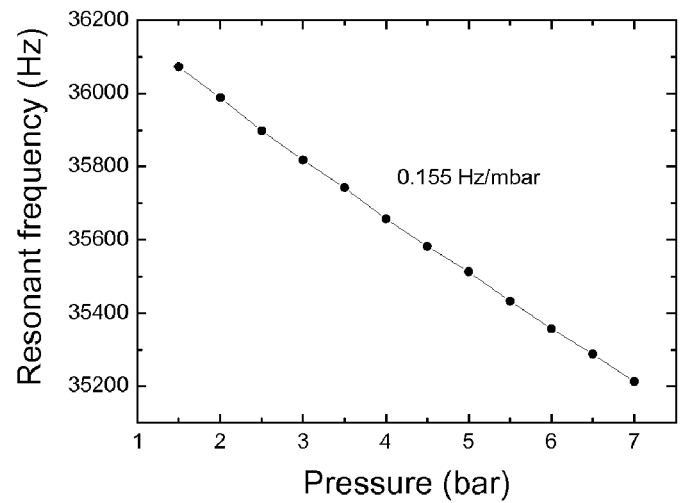
FIG. 18: Variation of first resonant frequency of diamond/AlN micro-cantilever as a function of nitrogen pressure.

The variation of impedance and the resonant frequency of the first resonant mode as a function of the pressure at room temperature are presented in FIG. 17 and FIG. 18, respectively. The impedance modulus and the phase shift amplitude decrease, as well as the resonant frequency, with increasing pressure. The variation of the resonant frequency exhibits a linear behavior as a function of the pressure. The variations of the impedance and the resonance frequency with nitrogen pressure are due to variation of the drag force that the gas applied onto the oscillating cantilever and which is a function of the viscosity and density of the gas. The sensitivity of the cantilever in nitrogen is 0.155 Hz/mbar. Assuming the resonant frequency can be measured with 6 digits accuracy, this pressure sensor has a sensitivity of ~1 mbar.

Diamond is a good material to obtain a high electromechanical coupling coefficient when it is used to make piezoelectric bimorph micro-cantilever sensors. This nano-diamond layers and low stress AlN films were grown to make a diamond AlN micro-cantilever. The resonant frequencies of this cantilever were measured in a vacuum. These values were in good agreement with theoretical values. The variation of the first resonant frequency with nitrogen pressure at room temperature was measured and showed that the resonant frequency varies linearly with the pressure with a sensitivity of 0.155 Hz/mbar.

EXAMPLE

Figure 19:
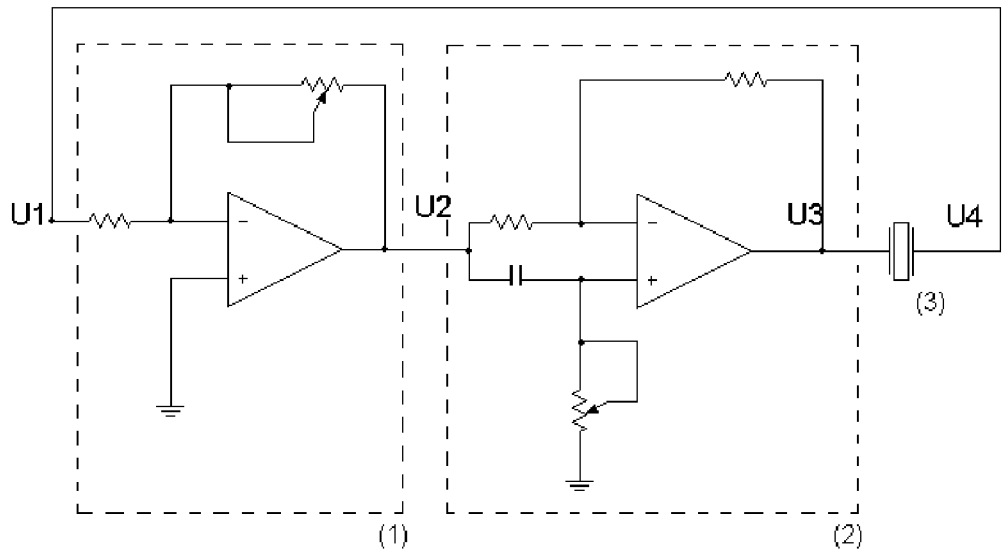
FIG. 19: Circuitry to oscillate the piezoelectric bimorph cantilever

The circuit that was used to oscillate the piezoelectric bimorph cantilever in the experiments is presented in FIG. 19. The first portion of the circuit (1) is to amplify the signal coming from the cantilever in such a way that the gain of the whole electrical loop is $\geq 1$ (first oscillation condition). The second part (2) is used to shift the phase of the signal coming from the cantilever (and amplified by the first stage) such that the total phase shift of the electrical loop (including the cantilever) is $2\pi$ (second oscillation condition).

The frequency generated by the oscillator has to be measured. One possibility is to use a frequency counter. The frequency counter can be seen as relatively slow since it measures on a time period which needs to be larger to achieve better resolution. This measurement is rather slow when a high resolution is needed.

Another possibility is to measure the period of a signal and calculate the frequency. Another frequency measurement may be carried out by measuring the period of the signal, and then computing the resonant frequency (f=1/T).

The invention claimed is:

1. A sensor for measuring at least two physical parameters in an environment comprising at least one of a gas and a liquid, comprising:
   a piezoelectric bimorph cantilever comprising at least a first layer, a piezoelectric layer, and two electrodes;
   a support on which the piezoelectric bimorph cantilever is mounted;
   electrical connections to the electrodes of the piezoelectric bimorph cantilever;
   means for vibrating the piezoelectric bimorph cantilever with the electrodes;
   means for measuring an output signal of the electrodes;
   means for determining the resonant frequencies of at least two resonance modes based on the output signal of the electrodes; and
   means for determining at least two physical parameters of the environment, each based on a combination of the resonant frequencies.

2. The sensor of claim 1, wherein the first layer of the piezoelectric bimorph cantilever is selected from the group consisting of silicon (Si), silicon nitride (SiN), silicon carbide (SiC), diamond, and silicon oxide ($SiO_2$).

3. The sensor of claim 1, wherein the piezoelectric layer of the piezoelectric bimorph cantilever comprises a material selected from the group consisting of Lead Zirconate Titanate (PZT), zinc oxide (ZnO), aluminum nitride (AlN), and barium titanium oxide ($BaTiO_3$).

4. The sensor of claim 1, wherein the electrodes of the piezoelectric bimorph cantilever comprise a material selected from the group consisting of gold (Au), aluminum (Al), platinum (Pt), and titanium nitride (TiN).

5. The sensor of claim 1, further comprising an adhesion layer positioned between the electrode material and at least one of the first layer and the piezoelectric material.

6. The sensor of claim 5, wherein the adhesion layer comprises titanium (Ti).

7. The sensor of claim 1, wherein the piezoelectric bimorph cantilever further comprises a layer for binding at least one of a biological species and a chemical species.

8. The sensor of claim 1, wherein means for vibrating the piezoelectric bimorph cantilever comprises an AC voltage source.

9. The sensor of claim 1, wherein means for measuring the output signal of the electrodes comprises an impedance analyzer.

10. The sensor of claim 1, wherein means for determining the resonant frequencies comprises a frequency-selective network.

11. The sensor of claim 10, wherein the frequency-selective network is mounted on a support on which the piezoelectric bimorph cantilever is mounted.

12. The sensor of claim 1, further comprising a protective housing disposed about the piezoelectric bimorph cantilever.

* * * * *